(12) United States Patent
Reyes et al.

(10) Patent No.: US 8,904,853 B2
(45) Date of Patent: Dec. 9, 2014

(54) METHOD OF TESTING PARTICULATES USED IN FRACTURING FLUIDS

(75) Inventors: Enrique A. Reyes, Duncan, OK (US); Jimmie D. Weaver, Duncan, OK (US); Richard D. Rickman, Duncan, OK (US); Hongyu Luo, Duncan, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 441 days.

(21) Appl. No.: 13/431,066

(22) Filed: Mar. 27, 2012

(65) Prior Publication Data

US 2012/0180551 A1 Jul. 19, 2012

Related U.S. Application Data

(62) Division of application No. 12/574,054, filed on Oct. 6, 2009, now Pat. No. 8,307,897.

(60) Provisional application No. 61/104,610, filed on Oct. 10, 2008, provisional application No. 61/104,620, filed on Oct. 10, 2008, provisional application No. 61/104,624, filed on Oct. 10, 2008, provisional application No. 61/104,629, filed on Oct. 10, 2008.

(51) Int. Cl.
*G01N 15/00* (2006.01)
*C09K 8/80* (2006.01)

(52) U.S. Cl.
CPC ............... *G01N 15/00* (2013.01); *C09K 8/805* (2013.01); *Y10S 507/901* (2013.01)
USPC ............ 73/61.71; 73/865.6; 73/866; 507/901

(58) Field of Classification Search
CPC ............................... G01N 15/00; G01N 15/08
USPC ............ 73/38, 61.71, 865.6, 866; 702/11, 12
See application file for complete search history.

(56) References Cited

U.S. PATENT DOCUMENTS

| | | | |
|---|---|---|---|
| 4,232,740 A | 11/1980 | Park | |
| 4,323,124 A | 4/1982 | Swan | |
| 4,460,627 A | 7/1984 | Weaver et al. | |
| 4,585,064 A | 4/1986 | Graham et al. | |
| 4,791,822 A * | 12/1988 | Penny | 73/865.6 |
| 4,848,145 A * | 7/1989 | Blaschke et al. | 73/152.55 |
| 5,018,396 A * | 5/1991 | Penny | 73/865.6 |
| 5,211,235 A | 5/1993 | Shu et al. | |
| 5,604,184 A | 2/1997 | Ellis et al. | |
| 7,387,161 B2 * | 6/2008 | Abass et al. | 166/280.1 |
| 8,443,885 B2 * | 5/2013 | Rickman et al. | 166/294 |
| 2006/0260808 A1 | 11/2006 | Weaver et al. | |
| 2007/0021309 A1 * | 1/2007 | Bicerano | 507/219 |
| 2007/0066491 A1 * | 3/2007 | Bicerano et al. | 507/117 |
| 2007/0079965 A1 | 4/2007 | Nguyen et al. | |
| 2007/0137859 A1 * | 6/2007 | Abass et al. | 166/250.1 |
| 2007/0289781 A1 * | 12/2007 | Rickman et al. | 175/65 |
| 2008/0135245 A1 | 6/2008 | Smith et al. | |
| 2008/0257545 A1 * | 10/2008 | Abass et al. | 166/250.01 |
| 2009/0300846 A1 | 12/2009 | Chaffee | |
| 2009/0300847 A1 | 12/2009 | Chan | |
| 2009/0306898 A1 * | 12/2009 | Anschutz et al. | 702/11 |
| 2010/0093566 A1 | 4/2010 | Reyes et al. | |

FOREIGN PATENT DOCUMENTS

| | | |
|---|---|---|
| CA | 2763680 A1 | 6/2008 |
| WO | 2005100007 A2 | 10/2005 |

OTHER PUBLICATIONS

Official Action for Australian Patent Application No. 2009300848 dated Jan. 10, 2014.
Weaver et al, Fracture-Related Diagenesis May Impact Conductivity, 2007, SPE Journal, pp. 272-281, XO002563499.
Official Action for EP Patent Application No. 09 736 634.8 dated Apr. 10, 2014.
Official Action for Canadian Patent Application No. 2,739,405 dated Feb. 5, 2013.

* cited by examiner

*Primary Examiner* — Hezron E Williams
*Assistant Examiner* — Nathaniel Kolb
(74) *Attorney, Agent, or Firm* — McDermott Will & Emery LLP; Craig W. Roddy

(57) ABSTRACT

Methods comprising: placing particulates in a test column; adding a fluid medium comprising a salt solution to the test column; placing the column under test conditions, wherein the test conditions comprise target temperature and target pressure; maintaining test conditions for a target test duration; and, analyzing the particulates. Some methods also measure a permeability value of the column after placing particulates in a test column and before placing the column under test conditions; continuously flow the salt solution through the particulates during the test; measure a permeability value after maintaining the test conditions for the target test duration; and, calculate a retained permeability value.

13 Claims, No Drawings

METHOD OF TESTING PARTICULATES USED IN FRACTURING FLUIDS

CROSS-REFERENCE TO RELATED APPLICATIONS

This application claims benefit of U.S. Provisional Patent Application Ser. Nos. 61/104,610, 61/104,620, 61/104,624, and 61/104,629, each filed Oct. 10, 2008, each of which is herein incorporated by reference. This application is a divisional of U.S. patent application Ser. No. 12/574,054 which is hereby incorporated by reference.

This application is related to U.S. patent application Ser. No. 12/574,037, entitled "Additives to Suppress Silica Scale Build-up," by Reyes et al., U.S. patent application Ser. No. 12/574,018, entitled "Ceramic Coated Particulates," by Reyes et al., and U.S. patent application Ser. No. 12/573.999, entitled "Prevention of Water Intrusion into Particulates," by Nguyen et al., filed on the same day herewith, which are hereby incorporated by reference in their entirety.

BACKGROUND

The present disclosure relates to treatments and compounds useful in subterranean formations, and, at least in some embodiments, to fracturing treatments and compounds wherein particulates and/or surfaces may be subject to water intrusion.

In the production of fluids, such as hydrocarbons or water, from a subterranean formation, the subterranean formation should be sufficiently conductive to permit the flow of desirable fluids to a well bore penetrating the formation. Among others, hydraulic fracturing may be a useful treatment for increasing the conductivity of a subterranean formation. Hydraulic fracturing operations generally may involve pumping a treatment fluid (e.g., a fracturing fluid or a "pad fluid") into a well bore that penetrates a subterranean formation at a sufficient hydraulic pressure to create or enhance one or more pathways, or "fractures," in the subterranean formation. Enhancing a fracture generally involves extending or enlarging a natural or pre-existing fracture in the formation. These fractures generally increase the permeability of that portion of the formation. The treatment fluid may comprise particulates, including proppant particulates that are deposited in the resultant fractures. The particulates are thought to help prevent the fractures from fully closing upon release of the hydraulic pressure, forming conductive channels through which fluid may flow between the formation and the well bore.

It is generally believed that the surfaces of particulates generally comprise minerals, which may react with other substances (e.g., water, minerals, treatment fluids, and the like) that reside in the subterranean formation in chemical reactions caused, at least in part, by conditions created by mechanical stresses on those minerals (e.g., fracturing of the mineral surfaces or the compaction of particulates). These reactions are herein referred to as "stress-activated reactions" or "stress-activated reactivity." One type of these stress-activated reactions may be diageneous reactions. As used herein, the terms "diageneous reactions," "diageneous reactivity," and "diagenesis" include chemical and/or physical processes that, in the presence of water, move a portion of the mineral in a particulate and/or convert a portion of the mineral in a particulate into some other form. A mineral that has been so moved or converted is herein referred to as a "diageneous product" or "diagenic product." Any particulate comprising a mineral may be susceptible to these diageneous reactions, including natural silicate minerals (e.g., quartz), man-made silicates and glass materials, metal oxide minerals (both natural and man-made), and the like.

Two of the principal mechanisms that diagenesis reactions are thought to involve are "pressure dissolution" and "precipitation processes." Where two water-wetted mineral surfaces are in contact with each other at a point under strain, the localized mineral solubility near that point may increase, causing the minerals to dissolve. Minerals in solution may diffuse through the water film outside of the region where the mineral surfaces are in contact (e.g., the pore spaces of a particulate pack), where they may precipitate out of solution. The dissolution and precipitation of minerals in the course of these reactions may reduce the conductivity of a particulate pack, inter alia, by clogging the pore spaces in the particulate pack with mineral precipitate and/or collapsing the pore spaces by dissolving solid mineral in the "walls" of those pore spaces. In other instances, minerals on the surface of a particulate may exhibit a tendency to react with substances in the reservoir, formation, and/or treatment fluids that are in contact with the particulates, such as water, gelling agents (e.g., polysaccharides, biopolymers, etc.), and other substances commonly found in these fluids. Molecules from such substances may become anchored to the mineral surface of the particulate. These types of reactivity may further decrease the conductivity of a subterranean formation, inter alia, through the obstruction of conductive fractures in the formation by any molecules that have become anchored to the particulates resident within those fractures. Both types of reactions may generally require the presence of a fluid, such as water, to occur to any significant extent.

SUMMARY

The present disclosure relates to treatments and compounds useful in subterranean formations, and, at least in some embodiments, to fracturing treatments and compounds wherein particulates and/or surfaces may be subject to water intrusion.

One embodiment of the present invention provides a method. The method comprises providing a diagenesis source material in a subterranean formation. The method further comprises introducing a first plurality of particulates into the subterranean formation. The method further comprises allowing the diagenesis source material to consolidate at least a portion of the first plurality of particulates.

Another embodiment of the invention provides a method. The method comprises providing a diagenesis source material in a subterranean formation, wherein the diagenesis source material is substantially free of proppant. The method further comprises allowing the diagenesis source material to produce a porous structure in the subterranean formation.

Yet another embodiment of the invention provides yet another method. The method comprises placing particulates in a test column. The method further comprises adding a fluid medium comprising a salt solution to the test column. The method further comprises placing the column under test conditions, wherein the test conditions comprise target temperature and target pressure. The method further comprises maintaining test conditions for a target test duration. The method further comprises analyzing the particulates.

The features and advantages of the present invention will be apparent to those skilled in the art. While numerous changes may be made by those skilled in the art, such changes are within the spirit of the invention.

DESCRIPTION OF PREFERRED EMBODIMENTS

The present disclosure relates to treatments and compounds useful in subterranean formations, and, at least in some embodiments, to fracturing treatments and compounds wherein particulates and/or surfaces may be subject to water intrusion.

The term "coating" as used herein refers to at least a partial coating of some or all of the particulates. Neither complete nor substantial coverage of the particulates or mix of particulates is implied by the term "coating." Rather, a particulate may be coated if it has, for example, at least a partial coating.

The term "derivative" is defined herein to include any compound that is made from one of the listed compounds, for example, by replacing one atom in the listed compound with another atom or group of atoms, rearranging two or more atoms in the listed compound, ionizing one of the listed compounds, or creating a salt of one of the listed compounds. A derivative of a material may include, but is not limited to, a compound composition based on a plurality of base materials, a composite material, or an aggregated material of various compositions.

As used herein, the terms "diageneous reactions," "diageneous reactivity," and "diagenesis" include chemical and physical processes that, in the presence of water, move a mineral and/or convert a mineral into some other form. Examples of such minerals include, but are not limited to, oxides or hydroxides of zirconium, magnesium, aluminum, titanium, calcium, strontium, barium, radium, zinc, cadmium, boron, gallium, iron, or any other element suitable for forming a diagenic product. Such minerals may be found in a particulate, in a formation, and/or introduced into a formation as "diagenesis source material." A mineral that has been so moved or converted is herein referred to as a "diageneous product" or "diagenic product."

As used herein, the term "aqueous fluid interaction" includes a variety of possible interactions between an aqueous fluid and a particulate. Such interactions may include infiltration of the aqueous fluid into the particulate, for example, by infiltrating pores, voids, crevices, cracks, and/or channels at or near the surface of the particulate. Such interactions may also include diagenesis.

As used herein, the term "diffusion barrier" includes any sort of material, including a coating, on or proximate to a particle that impedes and/or prevents aqueous fluid interaction with the particle. For example, some diffusion barriers fill or coat pores, voids, crevices, cracks, or channels at or near the particle's surface to impede and/or prevent infiltration by the aqueous fluid. As another example, some diffusion barriers impede and/or prevent diagenesis.

As used herein, the term "diagenic protective materials" refers to one or more diagenic products that may be selectively promoted in order to form a diffusion barrier.

As used herein, the term "filler" or "filler material" means a particulate material that is capable of fitting within a pore, void, crevice, crack, or channel at or near the surface of a particulate or on surfaces within the porous matrix of the individual particulates.

As used herein, the term "relatively low molecular weight" refers to a molecular weight that would encompass monomers and short-chain polymers having physical dimensions from a few angstroms to several hundred nanometers.

As used herein, a "monolayer" refers to a coating of a material approximately one unit thick. For chemicals, this may mean a coating as thin as one molecule, and for particulate compositions, it may mean a coating one particulate grain deep.

As used herein, the terms "pores," "voids," "crevices," "cracks," and "channels" refer to features at or near the surface of a particulate. Any given particulate may have one or more pores, voids, crevices, cracks, or channels, or may be free of such features. One or more such features may be generally referred to as "surface features." The use of the terms in conjunction is in no way intended to indicate that all three must be present simultaneously, or at all, in order for the teachings of the present disclosure to apply.

As used herein, the terms "particle," "particulate," "proppant particulate," and "gravel" are all used to refer to either a single particle or a plurality of particles which may be used for supporting a fracture in an underground formation, for forming a proppant pack, or for use in forming a gravel pack. Such particles may be disposed in a subterranean formation, including in spaces in the rock itself, fractures within the rock, and/or a well bore penetrating the subterranean formation.

As used herein, the term "pack" or "particulate pack" refers to a collection of particulates within an enclosed volume, wherein the particulates may be juxtaposed and/or in contact with one another, and wherein pore spaces may be disposed between the particulates. Examples of "packs" may include "proppant packs," which may refer to a collection of proppant particulates within a fracture, and/or "gravel packs," which may refer to a grouping of particulates that are packed sufficiently close together so as to prevent the passage of certain materials through the pack.

The term "on-the-fly" is used herein to indicate that one flowing stream comprising particulates is introduced into another flowing stream comprising a hydrophobic coating agent so that the streams are combined and mixed to flow as a single stream. In some instances, the streams may be combined to flow as a single stream as part of an on-going treatment at the job site. Such mixing can also be described as "real-time" mixing.

If there is any conflict in the usages of a word or term in this specification and one or more patent or other documents that may be incorporated herein by reference, the definitions that are consistent with this specification should be adopted for the purposes of understanding this invention.

There are many advantages of the present invention, only some of which are mentioned here. One advantage of the present invention may be the prevention of migration of unconsolidated particulates within portions of subterranean formations, including within the rock itself, fractures within the rock, and/or a well bore penetrating the subterranean formation. For example, the methods of the present invention may be used to consolidate particulates placed into a subterranean fracture while maintaining permeability for the passage of a subterranean fluid. Alternatively, the present invention may be used to create a particulate pack downhole without the need for externally-provided particulate.

Another advantage of the present invention may be the ability to quickly and easily consolidate particulates. Particulate consolidation may be performed using a variety of techniques. In an embodiment, one or more compounds and methods may be used to promote a diagenesis reaction within a subterranean environment. The diagenesis reaction may be promoted using liquid or solid diagenesis source materials in a variety of forms, as will be discussed in more detail. In an embodiment, the diagenesis reaction may be promoted to consolidate particulates to form a particulate pack, a proppant pack, a gravel pack, or any other type of structure where a consolidated group of particulates would be useful. In an alternative embodiment, the diagenesis reaction may be promoted within a fracture or other subterranean space to promote the growth of a porous structure, which may be used to prop open a fracture, either with or without additional particulate materials.

A further advantage of the present invention may be the ability to at least partially coat the particulate with a very thin diffusion barrier that may impede aqueous fluid interactions. For example, in an embodiment in which a diffusion barrier is pre-coated onto a filler material, a monolayer of the filler material may be created when the particulate is exposed to the filler material. In another embodiment, a very thin layer of the filler material may be coated on the particulate through the use of relatively low molecular weight materials with one or more of the coating techniques disclosed herein.

Protecting particulates from damaging interactions with aqueous fluids may be achieved in several ways. In accordance with embodiments of the present invention, these generally may include treating a particulate with a diffusion barrier which acts to impede the particulate interaction with aqueous fluids during and/or after placement in the formation. The diffusion barrier may comprise one of several types of materials, including hydrophobic materials, diagenic protective materials, and various polymeric compositions. Some embodiments of the present invention may utilize filler material to fill the pores, voids, crevices, cracks, or channels that may be present in a particulate surface. Alternatively, a filler material may be used to generate and/or place the diffusion barrier. For example, a hydrophobic material may be used to coat a filler material, and the filler material may then generate a diffusion barrier (e.g., comprising a diageneous product) on the particulates. The filler material may fill the pores, voids, crevices, cracks, or channels on the particulate surface, resulting in a surface that may be more hydrophobic than the original particulate surface. Each of these materials and methods will be described in more detail below.

In an embodiment, diagenesis reactions may be promoted through the appropriate selection of diagenesis source materials placed and/or found in a subterranean formation. The reaction conditions in a subterranean formation desired to promote diagenesis reactions are usually determined by the geological properties specific to each formation. These may include, but are not limited to, the subterranean formation temperature and pressure, the formation fluid concentration and composition, and formation face composition. The formation face composition generally may determine the types of materials in a fluid in contact with the formation surface. For example, the ion concentration in an aqueous fluid in contact with a formation surface is generally the equilibrium concentration of the elements and salts making up the formation surface. Diagenesis may occur when the equilibrium is disturbed through the introduction of new materials. The types of additional materials introduced into the formation may determine the diagenic products and the formation conditions, which may affect, for example, a particular crystal structure of the diagenic products. In an embodiment, an appropriate selection of diagenesis source materials may be used to promote a specific crystal structure. In some embodiments, dense crystal structures may be promoted to add strength to a consolidated particulate pack or to create a porous material through which a fluid may flow.

Diagenesis reactions may be promoted through the use of various diagenesis source materials. In an embodiment, suitable diagenesis source materials may include any chemical that may produce an appropriate chemical concentration in a subterranean formation to obtain a desired diagenic product. In an embodiment, suitable diagenesis source materials used to promote diagenesis reactions may include, but are not limited to, oxides or hydroxides of zirconium, magnesium, aluminum, titanium, calcium, strontium, barium, zinc, cadmium, boron, gallium, iron, or any other element suitable for forming a diagenic product. Oxides or hydroxides of some or all of these metals may be commercially available from various sources. For example, Clay-Sol™, available from Halliburton Energy Services, Inc. of Duncan, Okla., is a hydroxy alumina additive for use with aqueous systems. The diagenesis source materials may be introduced into the formation as either a liquid solution or a solid material. Diagenesis source materials may be used in combination to achieve desired results. In an embodiment, a diagenesis source material that has a low solubility in an aqueous fluid may be desirable for the formation of a dense diagenic product.

One of ordinary skill in the art with the benefit of this disclosure will be able to determine which diagenesis source materials should be included to achieve a desired diagenic product based on, for example, formation conditions, formation chemistry, and a desired diagenic product and crystal structure. For example, the pH of the subterranean formation may affect the availability of certain materials as diagenesis source materials. In an embodiment, the formation conditions and chemistry may be determined from an analysis of the subterranean formation materials including, for example, core samples and formation fluid.

The particulates that may be used in embodiments of the present invention include any proppant or gravel particulates that may be used in a subterranean application. Suitable particulates may include sand, sintered bauxite, silica alumina, glass beads, etc. Other suitable particulates include, but are not limited to, sand, bauxite, garnets, fumed silica, ceramic materials, glass materials, polymer materials, polytetrafluoroethylene materials, nut shell pieces, seed shell pieces, fruit pit pieces, wood, composite particulates, proppant particulates, degradable particulates, coated particulates, gravel, and combinations thereof. Suitable composite materials may comprise a binder and a particulate material wherein suitable particulate materials may include silica, alumina, garnets, fumed carbon, carbon black, graphite, mica, titanium dioxide, meta-silicate, calcium silicate, kaolin, talc, zirconia, boron, fly ash, hollow glass microspheres, solid glass, and combinations thereof. In certain embodiments, the particles may comprise common sand. In some embodiments, a derivative of one or more of the particulate materials may also be used. Derivatives may include materials such as compounds, composite materials, and aggregated materials of various compositions. In some embodiments of the present invention, some or all of the particulates may be comprised of a diagenesis source material. In this embodiment, the particulates may comprise oxides or hydroxides of zirconium, magnesium, aluminum, titanium, calcium, strontium, barium, radium, zinc, cadmium, boron, gallium, iron, or any other element suitable for forming a diagenic product. Suitable particulates may take any shape including, but not limited to, the physical shape of platelets, shavings, flakes, ribbons, rods, strips, spheres, spheroids, ellipsoids, toroids, pellets, or tablets. Although a variety of particulate sizes may be useful in the present invention, in certain embodiments, particulate sizes may range from about 200 mesh to about 8 mesh.

Embodiments of particulates of the present invention may contain pores, voids, crevices, cracks, or channels at or near the surface. For example, SEM micrographs at high magnification may show that the surfaces of particles, such as particulates made from bauxite, may be laden with pores, voids, crevices, cracks, and channels. Without being limited by theory, it is believed that these pores, voids, crevices, cracks, or channels at or near the particulate surface may provide a direct path to allow a detrimental interaction between aqueous fluids and the particles that may lead to degradation of the particles under formation pressure and temperature.

In some embodiments, the particulates may be treated or coated with one or more suitable substances. Generally, the particulates may be treated or coated with any substance which is suitable for traditional particulate treatments. In certain embodiments, the particulates may be coated so as to impede the intrusion of water into the particulates. For example, the particulates may be coated and/or used as discussed in "Prevention of Water Intrusion Into Particulates" by Nguyen et al., U.S. patent application Ser. No. 12/573,999, "Additives to Suppress Silica Scale Build-up" by Reyes et al., U.S. patent application Ser. No. 12/574,037, and/or "Ceramic Coated Particulates" by Reyes et al., U.S. patent application Ser. No. 12/574,018, each filed on the same day herewith, and the entire disclosures of which are hereby incorporated by reference in their entirety. In an embodiment, a portion of the particulates may be coated so as to limit their diagenic reactivity while others may remain uncoated so as to provide a reaction site for the diagenesis source material.

The particle compositions used in some of the embodiments of the present invention may comprise at least one particulate and a diffusion barrier, which may comprise a hydrophobic, or water repellant, material. Diffusion barriers may be initiated by and/or formed from a variety of materials. For example, certain materials may initiate diffusion barriers in some embodiments of the present invention. Suitable materials may be any chemical agent capable of forming a hydrophobic coating on the surface of particulates. In certain embodiments, particles comprising a diffusion barrier may have a retained strength greater than or equal to about 30%, as discussed in more detail below. In some embodiments, such diffusion barriers may enhance the recovery of a reservoir, formation, and/or treatment fluid. In certain embodiments, a surfactant may be included in the coating material so as to improve the coating process. Suitable coating materials may include oligomeric materials, monomeric materials, oil-wetting compounds, and combinations thereof to provide at least a monomolecular film, which may make the mineral surfaces water-repellent or hydrophobic.

In one embodiment, a diffusion barrier may comprise the reaction products of a compound having a reactive silyl group. The diffusion barrier may be formed by forming a silicon oxide layer or hybrid organo-silicon oxide anchor layer from a humidified reaction product of silicon tetrachloride or trichloromethylsilane, followed by the vapor-deposition of a chloroalkylsilane. In another embodiment, the diffusion barrier may comprise a trimethylsilyl functional group. For example, if a fumed silica filler particle is used, the surface hydroxyl groups may be replaced with trimethylsilyl functional groups to form a hydrophobic filler particle. The diffusion barrier may also comprise silicones or siloxanes. In an embodiment, the diffusion barrier may comprise an organosilicon compound, which may include, for example, an organosiloxane, an organosilane, a fluoro-organosiloxane, and a fluoro-organosilane. The diffusion barrier may also comprise a polysiloxane or an organo-modified polysiloxane, which may include a di-betaine polysiloxane or a di-quaternary polysiloxane.

In another embodiment, a diffusion barrier may comprise polymers of a fluoroalkyl-group containing silane compound, and the polymers may include at least dimers and trimers of the silane compound. This diffusion barrier may be made by preparing a solution, the solution being produced by subjecting a fluoroalkyl-group contained silane compound to a hydrolysis and a condensation polymerization to produce at least dimers and trimers of the silane compound, coating the solution onto the surface of the particulate or filler material, and heating the material to cause the fluoroalkyl group in the solution to be bonded to the surface of the particulate solids so as to form a hydrophobic film on the material. In another embodiment, the diffusion barrier may comprise a fluoro-organosiloxane or a fluoro-organosilane compound, which may include, for example, 2-(n-perfluoro-octyl)-ethyltriethoxysilane and perfluoro-octyldimethyl chlorosilane.

In yet another embodiment, a diffusion barrier may comprise a polyamide. In still another embodiment, the diffusion barrier may comprise a silyl-modified polyamide.

In an embodiment, a diffusion barrier may comprise polytetrafluoroethylene, plant oils, hydrocarbons, copolymerized polyvinylidene chloride, or any other substance capable of hindering or preventing aqueous fluid penetration, permeation, or wetting of a particulate.

The filler material may comprise materials with particles of micrometer-size, sub-micrometer-size, nano-size, or a combination thereof. The filler material may be reinforcing or non-reinforcing. Filler materials may include, for example, fumed silica, fused silica, garnet powder, clay, mica, alumina, finely divided quartz powder, amorphous silicas, meta-silicates, calcium silicates, calcine, kaoline, talc, zirconia, fly ash, boron, carbon black, fumed carbon, graphite, diamond, silicone carbide, aluminum hydrates, metal nitrides (such as boron nitride, and aluminum nitrides), metal oxides (such as aluminum oxide, zinc oxide, titanium dioxide or iron oxide), and any combination thereof. In another embodiment, the filler material may comprise metal particles, such as aluminum, zirconium, titanium, or derivatives thereof. In one embodiment, the average diameter of the filler material particles may be less than about 20 micrometers. In one embodiment, the average filler material particle diameter may range from about 0.05 micrometers to about 10 micrometers, or from about 0.1 micrometers to about 10 micrometers. In another embodiment, the particles of filler material may have a size range of from about 0.1 micrometer to about 0.5 micrometers, or from about 0.2 micrometers to about 0.5 micrometers.

In accordance with embodiments of the present invention, the filler material particle size may be chosen, among other purposes, to achieve a coating of a particulate including the pore spaces on the particulate surface. The choice of a filler material particle size may be based upon a consideration of the surface characteristics of the particulate, which may be based on the choice of particulate material, crystal structure, and/or other characteristics. In an embodiment, the filler material particle size may be such that the maximum filler material particle size may be at least equal to, and, in some embodiments, less than, the expected diameter of a pore, void, crevice, crack, or channel at or near the surface of the particulate. Consideration of any additional coating thickness that the coating material may add to the filler material also may be a consideration in choosing a filler material having certain particle sizes and shapes.

In some embodiments of the present invention, some or all of the filler material may be comprised of a material useful for promoting a diagenesis reaction, such as a diagenesis source material. For example, the filler material may comprise oxides or hydroxides of zirconium, magnesium, aluminum, titanium, calcium, strontium, barium, radium, zinc, cadmium, boron, gallium, iron, or any other element suitable for forming a diagenic product.

In an embodiment, the filler material may comprise certain metallic compositions that may have the ability to fill the pores, voids, crevices, cracks, or channels of the particulates, which, among other things, may limit the interaction between the particulates and aqueous fluids. The metallic compositions may have physiochemical properties that may render the dissolution in aqueous fluids negligible under certain conditions. The metallic compositions may be chemically resistant. For example, certain metallic compositions may be capable of forming diagenic protective materials when placed in contact with reservoir, formation, and/or treatment fluids downhole. In an embodiment, the metallic compositions may include, but are not limited to, metal alkoxides, organometallic compounds (such as metal esters) of aluminum, zirconium, titanium, antimony, silicon, tin, boron, chromium, iron, and rare earth element compounds. In another embodiment, the metallic compounds may include metal cationic cross linking agents selected from boron (such as boric acid, borax, metal borates including tetraborates, tetrafluoroborates, boron ore), aluminum, zirconium, titanium, and antimony. In some embodiments of the present invention, some or all of the metallic compositions may be comprised of a material useful for promoting a diagenesis reaction. In this embodiment, the proppant particulates may comprise oxides or hydroxides of zirconium, magnesium, aluminum, titanium, calcium, strontium, barium, radium, zinc, cadmium, boron, gallium, iron, or any other element suitable for forming a diagenic product.

In an alternative embodiment, polymeric materials that include the metallic elements also may be used to coat the particulates. For example, silicon polymers (such as polymethylsilsesquioxane, polydimethylsiloxanes, and polysiloxazane) or any other metallic polymer capable of being delivered in polymeric form may be used. In some embodiments, suitable monomeric compositions may be used to coat the particulates and then polymerized using an appropriate activator.

One of ordinary skill in the art, with the benefit of this disclosure, will be able to determine which metallic compound or polymeric composition should be included for a particular application based on, for example, formation chemistry, particulate composition, and the potential growth of diagenic protective materials. Without limiting the invention to a particular theory or mechanism of action, it is currently believed that the introduction of the metallic or polymeric compositions may be used to promote a protective layer of diagenic product around the particulate once the coated particulate is placed within the formation. In an embodiment, the coating may be a diagenesis source material and may be used to create a diagenic product in a subterranean formation. For example, a silicon-based compound may be used to promote the growth of silicates when placed in contact with an aqueous fluid at formation conditions. For a properly placed silicon compound within the pores, voids, crevices, cracks or channels of a particulate, the silicate growth may fill the pores, voids, crevices, cracks, or channels, thereby limiting the interaction between the aqueous fluid and the interior of the particulate. In an embodiment, the diagenic product may also grow between individual proppant particulates to act as a binder.

In an embodiment, a diagenesis reaction may be promoted in a subterranean formation using several methods. For example, a liquid or solid diagenesis source material may be used to promote a diagenesis reaction. In an embodiment in which a solid diagenesis source material is used, the solid material may be introduced into the subterranean formation in several forms. For example, the solid diagenesis source material may be coated on a particulate, be a filler material, be a particulate, or comprise a portion of the particulates themselves.

In an embodiment, the diagenesis source material may be a coating on at least some of the particulates. In this embodiment, the diagenesis source material may be pre-coated onto the outside of at least some particulates. The particulates then may be placed in a subterranean formation where they may contact an aqueous fluid. Once in the formation, the diagenesis source material may react with the aqueous fluid to form a diagenic product that may bind the particulates together resulting in a conglomeration. This method may be useful in a subterranean formation for forming particulate conglomeration that may be, for example, a particulate pack such as a proppant pack or a gravel pack.

In some embodiments, some or all of the particulates may be composed of a diagenesis source material. If a portion of the particulates are comprised of diagenesis source material, the remaining particulates may be composed of a different material, subject to a diffusion barrier, coated with a protective coating, or any combination thereof. The particulates may be premixed offsite, mixed at the well site, or mixed on-the-fly. The mixture may be introduced into a subterranean formation to allow the diagenesis reactions to occur. For example, a portion of the particulates placed in a subterranean formation may be comprised of a diagenesis source material. The remaining particulates may be subject to a diffusion barrier and/or coated with a hydrophobic coating material. Once placed in a formation, the particulates comprising a diagenesis source material may be partially or wholly transformed into a diagenic product. The diagenic product may bind the remaining particulates into a conglomeration while, at the same time, leaving interstitial spaces between the remaining particulates to increase the permeability. Such an embodiment may be useful for forming an improved permeability particulate pack in a subterranean fracture. In some embodiments, the volume of interstitial space created by the reaction of some or all of the diagenesis source material may be controlled based on the solubility of the diagenesis source material in the formation and the initial size of the diagenesis source material particulates. In one embodiment, the particulates composed of a diagenesis source material may be present in an amount ranging from about 0.1% by weight to about 50% by weight. In an alternative embodiment, the particulates composed of a diagensis source material may be present in an amount ranging from about 0.2% to about 15% by weight.

In an embodiment, the particulates may be composed of a diagenesis source material. In this embodiment, the particulates may be introduced into a subterranean formation and allowed to react with an aqueous fluid. For example, the particulates may comprise an alumina material that may react with an aqueous formation fluid. A diagenic product may form between the particulate grains and act to bind the particulates together. In an embodiment, this method may be used to form a particulate pack in a fractured formation.

In another embodiment, a filler material that comprises a diagenesis source material may be used. In this embodiment, a filler material that comprises a diagenesis source material may be provided and combined with a particulate. The particulate may be subject to a diffusion barrier which acts to inhibit reactions with an aqueous fluid. The mixture then may be introduced into a subterranean formation and allowed to react with an aqueous fluid. In this embodiment, the filler material may be mixed with the particulates offsite, at the well site, or on-the-fly. In another embodiment, the particulates may be introduced into the formation followed by an introduction of the filler material into the formation. The filler material may be introduced at a point in time removed from the initial placement of the particulates in the formation. In one embodiment, a carrier fluid may be used to carry the filler material into particulates that have been placed in a subterranean formation. In an embodiment, the particulates may be used to form a particulate pack, such as a proppant pack, a gravel pack, or a combination of both.

In still another embodiment, a fluid comprising a diagenesis source material may be used to create a diageneous reaction. In this embodiment, a fluid containing a diagenesis source material may be introduced into a subterranean formation. The diagenesis source material may interact with an aqueous fluid or with other materials in the subterranean formation to form a diagenic product. The diagenic product may act, among other things, to produce a porous structure and/or consolidate particulates in the formation. In some embodiments, particulates subject to consolidation may have been introduced into the formation during previous treatments, introduced into the formation in conjunction with the diagenesis source material treatment, and/or originated in the formation. In one embodiment, one or more particulates may be subject to a diffusion barrier. In another embodiment, a particulate may be introduced into a subterranean formation followed by the introduction of a fluid containing a diagenesis source material. The diagenesis source material may act to consolidate the particulates to some degree. In an embodiment, a fluid comprising a diagenesis source material may be used to treat particulate that was previously placed in a subterranean formation. In an embodiment, the particulates may be used to form a particulate pack, such as a proppant pack, a gravel pack, or a combination of both. In another embodiment, the diagenesis source material may form a porous structure comprising diagenic products, while being substantially free of proppant.

In practicing certain embodiments of the present invention, the process of mixing the particulates and the diagenesis source material may be performed at any stage of the particulate preparation and/or use. This mixing may be accomplished in treatments performed prior to transporting the particulates to a well site, at the well site, or in a treatment performed "on-the-fly." One such on-the-fly mixing method may involve continuously conveying the particulates and the diagenesis source material (e.g., a filler material comprising a diagenesis source material) to a mixing vessel, for example, using a sand screw. Once inside the mixing vessel, the particulates may be contacted with the diagenesis source material and continuously removed from the mixing vessel. In that situation, the sand screw may be used both to aid in mixing the particulates with the diagenesis source material and to remove the diagenesis source material from the mixing tank. Batch or partial batch mixing may also be used to accomplish such mixing at a well site prior to introducing the particulates into a subterranean formation, in accordance with embodiments of the present invention.

One embodiment of the present invention provides a method. The method comprises providing a diagenesis source material in a subterranean formation. The method further comprises introducing a first plurality of particulates into the subterranean formation. The method further comprises allowing the diagenesis source material to consolidate at least a portion of the first plurality of particulates. In some embodiments, this method may be useful in the recovery of fluids from the subterranean formation. The fluids being recovered may be a fluid previously introduced into the subterranean formation, an aqueous reservoir and/or formation fluid, a hydrocarbon fluid, or a combination thereof. This embodiment may also be used as a subsequent treatment method to treat a proppant or gravel pack that has previously been placed in a formation and may benefit from being conglomerated.

Another embodiment of the invention provides a method. The method comprises providing a diagenesis source material in a subterranean formation, wherein the diagenesis source material is substantially free of proppant. The method further comprises allowing the diagenesis source material to produce a porous structure in the subterranean formation. In some embodiments, this method may be useful in the recovery of fluids from the subterranean formation. The fluids being recovered may be a fluid previously introduced into the subterranean formation, an aqueous reservoir and/or formation fluid, a hydrocarbon fluid, or a combination thereof. This embodiment may also be used as a subsequent treatment method to treat a proppant or gravel pack that has previously been placed in a formation and may benefit from being conglomerated.

Yet another embodiment of the invention provides yet another method. The method comprises placing particulates in a test column. The method further comprises adding a fluid medium comprising a salt solution to the test column. The method further comprises placing the column under test conditions, wherein the test conditions comprise target temperature and target pressure. The method further comprises maintaining test conditions for a target test duration. The method further comprises analyzing the particulates. In some embodiments, this method may be useful to analyze and/or quantify the effects of other methods disclosed herein.

In order to quantify the mechanical strength of the particulates and permeability of the particulate pack, both before and after exposure to formation conditions and fluids, several test procedures may be utilized to determine various particulate properties. The first test method studies temperature-promoted diagenesis of a particulate pack by exposing a particulate pack to a flowing solution of simulated formation fluid at an approximate formation temperature. The second procedure studies stress/temperature-promoted diagenic growth through exposure of a particulate pack to a static flow environment under simulated formation pressures and temperatures. The mechanical strength of individual particulates may be measured before and after the test procedures to determine the percentage of particulate strength lost due to exposure to formation temperature or pressure. Alternatively, the permeability of the particulate pack may be measured before and after the temperature-promoted diagenesis test in order to determine a retained permeability value for the particulate pack. As would be understood by one of ordinary skill in the art with the benefit of this disclosure, expected subterranean formation conditions (e.g., temperature, pressure, formation fluid composition) for a selected subterranean formation will determine the appropriate formation conditions for test procedures.

In the temperature-promoted diagenesis test procedure, deionized water may first be heated to a test temperature of between about 200 degrees Fahrenheit (° F.) and about 600° F. by passing it through a heat exchanger coil. Simulated formation fluid may be formed by passing the deionized water through multiple packs of crushed formation material arranged in series. The number of formation packs required for the test may vary such that the simulated formation fluid leaving the last pack may be in equilibrium with the crushed formation material. Through experimentation, the typical number of formation packs may generally be between about 1 and about 10. Crushed formation material may be screened to remove fines and an approximately 8/35 mesh fraction may be used in the formation packs.

In an embodiment, once a simulated formation fluid in equilibrium with the crushed formation material is obtained, the simulated formation fluid may be directed to a column containing a particulate pack. The temperature in the particulate pack may be maintained at an approximate formation temperature between about 200° F. and about 600° F., which approximately corresponds to the temperature of the deionized water first entering the system. A flow rate of simulated formation fluid may be maintained at approximately 1 milliliter per minute during the test.

The flow test may be maintained for between about 10 to about 200 days, and in an embodiment, for at least about 20 days. After this time, the particulate pack may be disassembled in order to test the mechanical properties of individual particles, as discussed in more detail below. For example, surface and compositional analysis may be made after disassembly to determine what types of materials are being formed under the simulated formation conditions. A permeability test may also be performed at this time. In this test, the permeability of the particulate packs may be measured at room temperature prior disassembly of the particulate pack. The measured permeability of the pack may then be compared with an initial permeability measurement made of the pack at room temperature before the pack is placed in the testing apparatus. Comparing the initial permeability measurement with the permeability measurement obtained after the pack is subjected to the test conditions may allow for a retained permeability to be calculated.

The stress/temperature-promoted diagenesis test method may involve the testing of the particulate pack under static flow conditions at approximate formation pressures and temperatures. In this method, a pack of particulates may be loaded in a test cell and filled with a salt solution. The test cell may be loaded from between about 0.5 pounds per square foot (lb/ft$^2$) of particulates to about 3.0 lb/ft$^2$ of particulates. In an embodiment, an approximately 2% KCl solution may be used as the fluid medium. Formation wafers, either manufactured from formation core material or from rock outcrop material, may be placed above and below the particulate pack in the test column. The system may then be shut in and placed under simulated formation pressure and heated to approximate formation temperatures. In an embodiment of this method, the temperature may be maintained at between about 100° F. and about 550° F. In another embodiment, the temperature may be maintained at between about 100° F. and about 350° F. The pressure may be maintained at between about 2,000 psi and about 10,000 psi. In another embodiment, the pressure may be maintained at between about 5,000 psi and about 8,000 psi. In an embodiment, the test may be conducted for between about 1 to about 50 weeks, and in another embodiment, the test may be conducted for at least about 4 weeks (about 28 days).

Upon completion of the stress/temperature-promoted diagenesis test, the test cell may be disassembled and the particulate pack removed for testing. As with the flow test method, additional tests may also be performed at this time. For example, surface and compositional analysis may be made after disassembly to determine what types of materials are being formed under the simulated formation conditions. Alternatively, the resulting interstitial fluid may be analyzed to determine the relative solubility of the particulates under formation conditions.

Changes in the mechanical properties of the particulates obtained from either the stress/temperature-promoted diagenesis test or the temperature-promoted diagenesis test may be determined using a single-grain crush-strength analysis. The analysis may utilize a Weibull statistical analysis procedure based on a plurality of particulate crush samples. The crush test may be based on a uni-axial compressive point loading of a particle. Under a compressive loading in the uni-axial direction, a spherical particle may be under tension in directions perpendicular to the loading with a tensile stress, σ, calculated by $$\sigma = \frac{2.8F}{\pi d^2}$$

where d is the diameter of each particle and F is the load at failure.

A Weibull analysis may include a statistically significant number of crush samples, which may range from about 10 to about 50 individual crush samples, or from about 20 to about 40 individual crush samples. In an embodiment, a sample size of between about 25 and about 30 individual crush samples of particulates may be used in the analysis. All of the strength data points may then be sorted from low to high as $\sigma_1 < \sigma_2 < \sigma_3 < \ldots < \sigma_N$, where N represents the total number of samples. A probability of failure may be calculated from the equation:

$$P_f = \left(\frac{\# - 0.5}{N}\right)$$

where, as before, N is the total number of samples, for example about 30 samples, and # is the index number for the sorted strength values (e.g., 1 through N). A linear plot may be obtained by plotting $$\ln\left(\ln\left(\frac{1}{1 - P_f}\right)\right) \text{ vs } \ln(\sigma)$$

A Weibull distribution may be found by linear fitting and generating an equation:

$$\ln\left(\ln\left(\frac{1}{1 - P_f}\right)\right) = m\ln\left(\frac{\sigma}{\sigma_0}\right)$$

where m is the Weibull modulus and $\sigma_0$ is the characteristic strength. The strength will tend to increase along with the reliability of the strength calculation when the $\sigma_0$ and m values increase. The characteristic strength changes in the particulates may then be determined. By comparing the characteristic strength of the particulates prior to exposure to the simulated formation fluid with the characteristic strength of the particulates after exposure to the simulated formation fluid, a retained strength value may be calculated from the equation:

$$\sigma_{0 \text{ retained}} = \left(\frac{\sigma_{0 \text{ exposed}}}{\sigma_{0 \text{ unexposed}}}\right)$$

where, $\sigma_{0 \text{ exposed}}$ is the characteristic strength of the particles after exposure to the simulated formation fluid, and $\sigma_{0 \text{ unexposed}}$ is the characteristic strength of the particles prior to exposure. Similarly, a retained permeability may be calculated by dividing the permeability measured at the end of the temperature-promoted diagenesis test with the permeability measured at the beginning.

In an embodiment, a single set of test conditions may be utilized for comparison of different sets of sets of particles comprising diffusion barriers and/or filler materials. The retained strength value is defined to be measured by the stress/temperature-promoted diagenesis test. In this method, a pack of particulates is loaded in a test column and filled with a salt solution comprising an approximately 2% KCl solution. The test cell is loaded with about 2 lb/ft$^2$ of particulates. Formation wafers are placed above and below the particulates in the test cell. The system is then shut in and placed under a pressure that is approximately equal to the pressure expected in the formation in which the particulates are expected to be placed. The temperature may be maintained at a temperature that is approximately equal to the formation temperature where the particulates are expected to be placed. For example, the system may be placed under simulated formation pressure of about 9000 psi and temperature of about 250° F. These conditions are then maintained for about 28 days.

Upon completion of the stress/temperature-promoted diagenesis test, the test cell is disassembled and the particulate matrix removed for testing. Changes in the mechanical properties of the particulates are obtained using particulates tested using the stress/temperature-promoted diagenesis test. The analysis utilizes a Weibull statistical analysis procedure based on a plurality of particulate crush samples, as discussed above. A single analysis includes a statistically significant number of samples, which may be between about 20 and about 40 samples, e.g., approximately 30 crushed samples of individual particles. However, in some instances, the sample size may vary such that the actual number of samples is smaller or larger in order to obtain a statistically significant number of samples. The characteristic strength changes in the particulates may then be determined. By comparing the characteristic strength of the particulates prior to exposure to the simulated formation fluid with the characteristic strength of the particulates after exposure to the simulated formation fluid, a retained strength value is calculated from the equation:

$$\sigma_{0\ retained} = \left(\frac{\sigma_{0\ exposed}}{\sigma_{0\ unexposed}}\right)$$

where, $\sigma_{0\ exposed}$ is the characteristic strength of the particles after exposure to the simulated formation fluid, and $\sigma_{0\ unexposed}$ is the characteristic strength of the particles prior to exposure.

Similarly, the retained permeability value of the particulate pack is defined to be measured by the temperature-promoted diagenesis test. In the temperature-promoted diagenesis test procedure, an initial permeability measurement is made of a particulate pack while the particulate pack is at room temperature. Deionized water is then heated to a test temperature of approximately 500° F. by passing it through a heat exchanger coil. Lower test temperatures may also be used depending on the specific particulate material and coating used. For example, one of ordinary skill in the art may determine that a lower test temperature is required in order to avoid thermal decomposition of the particulates, the diffusion barrier, or the filler material. Simulated formation fluid is formed by passing the deionized water through multiple packs of crushed formation material arranged in series. The number of formation packs required for the test may vary such that the simulated formation fluid leaving the last pack is in equilibrium with the crushed formation material at the flow rate used during the test of approximately 1 milliliter per minute. The typical number of formation packs is generally between about 2 and about 5. Crushed formation material is screened and an approximately 8/35 mesh fraction is used in the formation packs. The formation material is obtained by crushing a core withdrawn from a specific well during drilling or from dill cuttings obtained while a well is being drilled through a zone of interest.

The simulated formation fluid is then directed to a column containing a particulate pack. The temperature in the particulate pack is maintained at a temperature of about 500° F. A lower test temperature may be used depending on the specific particulate material and coating material used. For example, one of ordinary skill in the art may determine that a lower test temperature is required in order to avoid thermal decomposition of the particulates, the diffusion barrier, or the filler. A flow rate of simulated formation fluid is maintained at approximately 1 milliliter per minute during the test. The flow test is maintained for about 30 days. After this time, permeability of the particulate pack is measured prior to disassembly and after the particulate pack has been allowed to cool to room temperature, allowing for a retained permeability to be calculated from the equation:

$$Permeability_{retained} = \left(\frac{Permeability_{exposed}}{Permeability_{unexposed}}\right)$$

where, $Permeability_{exposed}$ is the permeability of the particles after exposure to the simulated formation fluid, and $Permeability_{unexposed}$ is the permeability of the particles prior to exposure.

Particulates prepared and tested according to the methods of the current invention using the characteristic conditions of the embodiment may exhibit a retained strength value of greater than about 20%. Alternatively, the particulates may exhibit a retained strength value of greater than about 60%. In still another embodiment, the particulates may exhibit a retained strength value of greater than about 80%. In yet another embodiment, the particulates may exhibit a retained strength value of greater than about 90%. In an embodiment, the particulates used to form a pack may be characterized by a retained permeability value of at least about 40%. In another embodiment, the particulates may be characterized by a retained permeability of at least about 60%. In still another embodiment, the particulates may be characterized by a retained permeability of at least about 80%. In some embodiments, the retained permeability may be at least about 99%.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method comprising:
measuring a first strength value for the particulates;
placing particulates in a test column;
adding a fluid medium comprising a salt solution to the test column;
placing the column under test conditions, wherein the test conditions comprise target temperature and target pressure;
maintaining test conditions for a target test duration;
measuring a second strength value for the particulates,
calculating a retained strength value; and,
analyzing the particulates.

2. The method of claim 1 further comprising:
measuring a permeability value of the column after placing particulates in a test column and before placing the column under test conditions;
continuously flowing the salt solution through the particulates during the test;
measuring a permeability value after maintaining the test conditions for the target test duration; and,
calculating a retained permeability value.

3. The method of claim 1 wherein the calculating a retained strength value comprises using a Weibull statistic analysis with a sample size of between about 10 and about 50 individual crush samples.

4. The method of claim 1 wherein the test conditions comprise a target pressure of between about 2,000 psi and about 10,000 psi.

5. The method of claim 1 wherein the test conditions comprise a target temperature of between about 100° F. and about 550° F.

6. The method of claim 1 wherein the target test duration comprises a period of from about 1 to about 50 weeks.

7. A method comprising:
measuring a first strength value for the particulates;
placing particulates in a test column;
creating a salt solution by passing deionized water at formation temperature through crushed formation material until the resulting salt solution is in equilibrium with the formation materials;
adding a fluid medium comprising the salt solution to the test column;
placing the column under test conditions, wherein the test conditions comprise target temperature and target pressure;
maintaining test conditions for a target test duration;
measuring a second strength value for the particulates;
calculating a retained strength value; and,
analyzing the particulates.

8. The method of claim 7 further comprising:
after placing the column under test conditions, continuously flowing the salt solution through the particulates during the test.

9. The method of claim 7 wherein the calculating a retained strength value comprises using a Weibull statistic analysis with a sample size of between about 10 and about 50 individual crush samples.

10. The method of claim 8 further comprising:
measuring a permeability value for the column after placing the particulates into the test column and before placing the column under test conditions;
measuring a permeability value for the particulates after maintaining the test conditions for the target test duration; and,
calculating a retained permeability value.

11. The method of claim 7 wherein the test conditions comprise a target pressure of between about 2,000 psi and about 10,000 psi.

12. The method of claim 7 wherein the test conditions comprise a target temperature of between about 200° F. and about 600° F.

13. The method of claim 7 wherein the target test duration comprises a period of from about 10 to about 200 days.

* * * * *